(12) United States Patent
Steadman Booker et al.

(10) Patent No.: US 11,435,488 B2
(45) Date of Patent: Sep. 6, 2022

(54) PHOTON COUNTING SPECTRAL CT (71) Applicant: KONINKLIJKE PHILIPS N.V., Eindhoven (NL)

(72) Inventors: Roger Steadman Booker, Aachen (DE); Christoph Jan Herrmann, Aachen (DE); Klaus Erhard, Hamburg (DE); Bernhard Johannes Brendel, Norderstedt (DE); Heiner Daerr, Hamburg (DE); Artur Sossin, Hamburg (DE); Axel Thran, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/053,890

(22) PCT Filed: May 7, 2019

(86) PCT No.: PCT/EP2019/061721
§ 371 (c)(1),
(2) Date: Nov. 9, 2020

(87) PCT Pub. No.: WO2019/215178
PCT Pub. Date: Nov. 14, 2019

(65) Prior Publication Data
US 2021/0382188 A1    Dec. 9, 2021

(30) Foreign Application Priority Data

May 8, 2018   (EP) .................................... 18171174

(51) Int. Cl.
*G01T 1/24*   (2006.01)
*A61B 6/03*   (2006.01)
*G01T 1/17*   (2006.01)

(52) U.S. Cl.
CPC .............. *G01T 1/247* (2013.01); *A61B 6/032* (2013.01); *G01T 1/17* (2013.01)

(58) Field of Classification Search
CPC ............ G01T 1/247; G01T 1/17; A61B 6/032
See application file for complete search history.

(56) References Cited

U.S. PATENT DOCUMENTS 9,176,238 B2   11/2015   Herrmann
9,759,822 B2   9/2017    Daerr
(Continued)

FOREIGN PATENT DOCUMENTS

WO   WO2012095710 A2   7/2012
WO   WO2017089363 A1   6/2017

OTHER PUBLICATIONS

PCT International Search Report, International application No. PCT/EP2019/061721, dated Aug. 5, 2019.

*Primary Examiner* — Hugh Maupin
(74) *Attorney, Agent, or Firm* — Larry Liberchuk (57) ABSTRACT

A radiation detector (100) adapted for detecting leakage currents is disclosed and comprises a direct conversion material (101) for converting incident radiation, at least one first electrode (108) and a plurality of second electrodes (103) connected to surfaces of the direct conversion material (101) for collecting each generated charges upon application of an electric field, at least one current measurement device (201), and a plurality of signal processing chains (210, 220, 230). Each signal processing chain comprises a readout unit (215, 216, 217, 218, 219) for discriminating between energy values with respect to the incident radiation, and a switching element (214) for sending signals on a first signal path (2141) electrically connecting one of the plurality of second electrodes with the readout unit, or on a second signal path electrically connecting the one of the plurality of second electrodes with an input to one of the at least one current (Continued)

measurement devices. A plurality of switching elements is configured to send signals on the second signal path for measuring a leakage current received at a corresponding plurality of second electrodes of the detector in the absence of incident radiation.

14 Claims, 4 Drawing Sheets

(56) References Cited

U.S. PATENT DOCUMENTS

| | | |
|---|---|---|
| 10,267,928 B2 | 4/2019 | Steadman Booker |
| 2004/0239377 A1 | 12/2004 | Tumer |
| 2006/0268135 A1 | 11/2006 | Lim |
| 2009/0290050 A1* | 11/2009 | Herrmann .............. H04N 5/361 |
| | | 348/243 |
| 2009/0290680 A1* | 11/2009 | Tumer .................... G01T 1/247 |
| | | 378/62 |
| 2014/0014818 A1 | 1/2014 | Cho |
| 2016/0170039 A1 | 6/2016 | Proksa |

\* cited by examiner

PHOTON COUNTING SPECTRAL CT

FIELD OF THE INVENTION

The present invention relates to the field of spectral computed tomography (CT) devices and methods, and is particularly concerned with photon counting spectral CT detector units and detection methods.

BACKGROUND OF THE INVENTION

Photon counting detector units in computed tomography (CT) applications offer one way of obtaining spectral readout information for a CT scanner measuring at more than one energy value. The performance of a CT system based on photon counting is strongly dependent on the temporal stability of all the readout components contributing to the final detection signal. Leakage currents over a photon counting detector, which are also variable over time and temperature, lead to artefacts in a reconstructed spectral CT image. Suppressing the leakage currents in a photon counting detector by detecting the average leakage current associated with a collection of radiation-blocking detector pixels and compensating the leakage currents of a collection of radiation-sensitive detector pixels is a technique that is known, but which does not fully use the available resources, as it is discarding some pixels. Therefore, there is a need for improved leakage current correcting photon counting detectors.

SUMMARY OF THE INVENTION

It is an object of embodiments of the present invention to provide a good system and method for correction of long term instability in photon counting spectral CT.

The above objective is accomplished by a method and device according to the present invention.

In a first aspect, the present invention relates to a radiation detector which is adapted for detecting leakage currents. The radiation detector comprises a direct conversion material for converting incident radiation into charges, at least one first electrode connected to a first major surface of the direct conversion material, and a plurality of second electrodes connected to a second major surface of the direct conversion material. Each of the first and second electrodes collects charges generated by incident radiation when an electric field between the first and second electrodes is applied. The radiation detector also comprises at least one current measurement device and a plurality of signal processing chains, each signal processing chain comprising a readout unit for discriminating between energy values with respect to the incident radiation and a switching element. A switching element is sending signals on a first signal path electrically connecting one of the plurality of second electrodes with the readout unit for discriminating between energy values, or on a second signal path electrically connecting the one of the plurality of second electrodes with an input to one of the at least one current measurement devices. A plurality of switching elements, included in the plurality of signal processing chains, is configured to send signals on the second signal path for measuring a leakage current received at a corresponding plurality of second electrodes of the detector in the absence of incident radiation.

It is an advantage of embodiments of the present invention that leakage currents can be measured with very high precision and without the need of optically blackening of pixels of a detector. Therefore, all the pixels may be available for readout of a radiation detection measurement and better spatial resolution and/or higher pixel counts are obtained. A clustering of pixels for measurement of the leakage current performs an averaging action on noise sources interfering with a leakage current measurement and thus a higher degree of precision and a higher signal-to-noise ratio is achieved for a measurement of a leakage current signal. Different clusters of pixels contributing to a leakage current measurement allow for spatial interpolation or extrapolation of leakage current signals across the sensitive area of a radiation detector.

It is an advantage of embodiments of the present invention that additional electronic signal processing circuitry dedicated to leakage current detection and compensation may be avoided, thus facing less restrictions on available electronics design area. If dedicated leakage current compensation circuitry is present, the present invention benefits from the fact that uncompensated residual leakage current signals are measurable with high precision and an enhanced further correction thereof is still possible. It is an advantage of embodiments of the present invention that a larger dynamic range of leakage current signals is measurable and cheaper CZT crystals, or other suitable conversion material, less demanding in their manufacturing process, may be used. An increase of leakage current signals due to degradation of the conversion material is taken account for by the larger dynamic measurement range for leakage currents.

Yet another advantage of embodiments of the present invention is that artefacts in reconstructed, energy-resolved images are reduced due to the detection and compensation of coherent shifts in the energy spectrum which are caused by time-varying and/or inhomogeneous leakage currents. Better energy resolution and/or pixel independent statistics may be obtained, and a baseline restoring unit may not be required.

The at least one direct conversion material of the radiation detector may be a CZT crystal. Cadmium zinc telluride (CZT) crystals are direct bandgap semiconductors which efficiently generated electron-hole pairs at room temperatures not requiring an adequate cooling system. CZT crystals contain elements with high atomic numbers leading to an increased photon absorption coefficient in this material. This is beneficial for the fabrication of thin detectors with high photon absorption.

The plurality of second electrodes may be arranged as an array of electrodes on the second major surface.

An array of electrodes is contacted more easily and may be a regularly structured, conductive attachment means forming the electrical interface with the signal processing chains of the pixels embedded in a semiconductor substrate. This lowers the risk of dead/non-responsive pixels in a detector. An array of electrodes also provides good spatial resolution of the detector.

The detector may further comprise a storage device for storing a measured leakage current. A stored value of the measured leakage current may thus be embedded in the raw image data acquired by the detector. This is useful if the measured leakage current is used as a parameter in an image reconstruction unit which reconstructs spectrally (energy) resolved images of a scanned object or patient from a set of raw image data, typically projections at different angles and for different slices. The storage device may also store a reference or calibration value for a leakage current to which a measured leakage current may be compared. This offers the possibility of an on-chip hardware correction of leakage currents and resulting shifts in the energy spectrum.

At least one current measurement device may comprise an analog-to-digital-converter. Analog-to-digital-converters may be designed for a large range of measurable current values at high precision and may be configurable for different ranges or precisions. They may be integrated in a compact way in the same semiconductor substrate as the signal processing chains associated with each detector pixel and provide stable operation during the time the leakage current is measured. Analog-to-digital-converters provide a digital representation of a measured leakage current suitable for further processing in digital electronics.

The signal processing chains may further comprise a leakage current detection unit and a leakage current compensation unit for signals sent on the first and the second signal path. In this case an output of the leakage current detection unit is connected to an input of the leakage current compensation unit and an output of the leakage current compensation unit is connected to the switching element.

This allows for a hardware pre-compensation of leakage currents at the pixel level at the time of detection, thus any additional postprocessing step may be discarded. This pre-compensation may be at a coarse level and not be very precise, which often reduces electronic design space and cost. Residuals of such a pre-compensation or residuals due to altering conditions under which such pre-compensation is performed may still be measured and used for later correction in accordance to the present invention.

In a second aspect, the present invention relates to a detector system comprising a plurality of radiation detectors according to the first aspect of the present invention.

A detector system may comprise an array of detectors for enabling a larger area of detection. Such detector system may therefore allow for larger viewing angles for incident radiation or larger scan volumes of scanned objects/patients. This potentially lowers the number of exposures required for a good quality scan and the scan is expedited.

Such detector system may also comprise a radiation source and an image reconstruction unit for reconstructing images of an object for which, if placed between the radiation source and the plurality of detectors, projection data for radiation traversing the object is obtained.

This is a typical arrangement for a scanning system, for instance a computed tomography scanning system. In such a scanning system an information on the measured leakage currents may be readily available for a particular detector/detector tile or arrays of detectors and may be used as an input to the image reconstruction unit for each scan. Therefore, improved reconstructed images may be available at higher qualities and more accurate energy resolutions more easily.

The image reconstruction unit may comprise a detector model which uses a measured leakage current for correcting spectral energy shifts.

This has the advantage that the measured leakage current may be used in a reconstruction method which takes into account the changing conditions, e.g. temperature changes, of the detector or detector system during a scan and compensates for it. As a result the presence of artefacts may be reduced or eliminated.

In a third aspect, the present invention relates to a method for performing a spectral CT scan. The method comprises the steps of collecting charges generated in direct conversion material in the absence of radiation, at a plurality of pixel electrodes, sending collected charge signals from the plurality of pixel electrodes to a common node, and measuring a leakage current at the common node. Thereafter a radiation signal is provided and signals received by each of the plurality of pixel electrodes are discriminated according to a set of energy threshold values. The number of occurrences of signals exceeding an energy threshold value for each of the plurality of pixel electrodes is counted, thus obtaining spectral (photon) counts. The method comprises the step of adjusting the energy threshold values used in the discrimination and/or the counting of the number of occurrences, based on the measured leakage current.

A plurality of pixel electrodes for which charge signals are collected and sent to a common node for measuring a leakage current may be different for repeated measurements of a leakage current at the common node.

This has the advantage that a leakage current of different regions of a detector may be measured separately from each other. The plurality of pixel electrodes may for instance only comprise the bulk pixels of a detector, for which a measured leakage current is expected to be different from a measured leakage current with respect to the edge pixels of a detector only. The plurality of pixel electrodes may be a checkerboard pattern or a random distribution of pixels of a detector or may correspond to the four quadrants of a pixel array of a detector. This allows for improved averaging effects for a leakage current measurement. Hot or dark pixels may be excluded from a leakage current measurement. Repeated, differently selected patterns for the plurality of pixel electrodes may improve the precision of a leakage current measurement and may cover the whole sensitive area of a detector. Selected patterns for the plurality of pixel electrodes may also be useful for performing spatial interpolation to obtain an estimated value of a leakage current for a pixel that was not contributing to the leakage current measurement.

The leakage current measured at the common node may be digitized. This makes the measured leakage current suitable for digital postprocessing or its use in digital processing units.

A leakage current may be measured at the common node again, when a radiation signal is not provided anymore.

Therefore spectral counts may be corrected even for changes in the incident radiation during exposure or for environmental changes, e.g. temperature changes, which occurred during the exposure and have an impact on the spectral counting.

A leakage current signal at the common node may be linearly estimated for times during which a radiation signal is provided. For these times a leakage current measurement is typically avoided to avoid prolonged scan times. Nevertheless, a leakage current signal may be estimated by interpolating between two measurements performed before and after each scan. An estimate for the leakage current may be obtained by interpolating linearly, by polynomial interpolation, spline interpolation, etc.

An estimate for the leakage current may take into account the measured photon flux, i.e. the history of measured spectral photon counts during a complete scan. This may improve the interpolated value for the leakage current.

An object image may also be reconstructed based on the spectral counts obtained for signals received by each pixel electrode, wherein reconstructing an object image comprises adjusting energy threshold parameters of a spectral model to compensate for spectral energy shifts derivable from the measured or estimated leakage currents.

Particular and preferred aspects of the invention are set out in the accompanying independent and dependent claims. Features from the dependent claims may be combined with features of the independent claims and with features of other dependent claims as appropriate and not merely as explicitly set out in the claims.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The above and other aspects of the invention will be apparent from and elucidated with reference to the embodiment(s) described hereinafter.

BRIEF DESCRIPTION OF THE DRAWINGS

The invention will now be described further, by way of example, with reference to the accompanying drawings, in which.

The drawings are only schematic and are non-limiting. In the drawings, the size of some of the elements may be exaggerated and not drawn on scale for illustrative purposes. The dimensions and the relative dimensions do not necessarily correspond to actual reductions to practice of the invention.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims.

The terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, directional terminology such as top, bottom, front, back, leading, trailing, under, over and the like in the description and the claims is used for descriptive purposes with reference to the orientation of the drawings being described, and not necessarily for describing relative positions. Because components of embodiments of the present invention can be positioned in a number of different orientations, the directional terminology is used for purposes of illustration only, and is in no way intended to be limiting, unless otherwise indicated. It is, hence, to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art.

It should be noted that the use of particular terminology when describing certain features or aspects of the invention should not be taken to imply that the terminology is being re-defined herein to be restricted to include any specific characteristics of the features or aspects of the invention with which that terminology is associated.

In the description provided herein, numerous specific details are set forth. However, it is understood that embodiments of the invention may be practiced without these specific details. In other instances, well-known methods, structures and techniques have not been shown in detail in order not to obscure an understanding of this description.

Definitions

A detector, in the context of the present invention, delivers a signal representative for impinging radiation. Radiation impinges on the detector, where it is converted into a measurable signal. The impinging radiation may be electromagnetic radiation of any type, e.g. visible light, UV light, infra-red light, X-rays, gamma rays.

A detector may comprise a plurality of pixels, possibly arranged in an array. A pixel of a detector, in the context of the present invention, refers to an element comprising a particular geometric, active region in a bulk direct conversion material as defined by a radiation-sensitive volume between a top electrode and a pixel electrode. The pixel may, via its pixel electrode, be electrically connected to a signal processing chain.

DETAILED DESCRIPTION OF THE EMBODIMENTS

Figure 1:
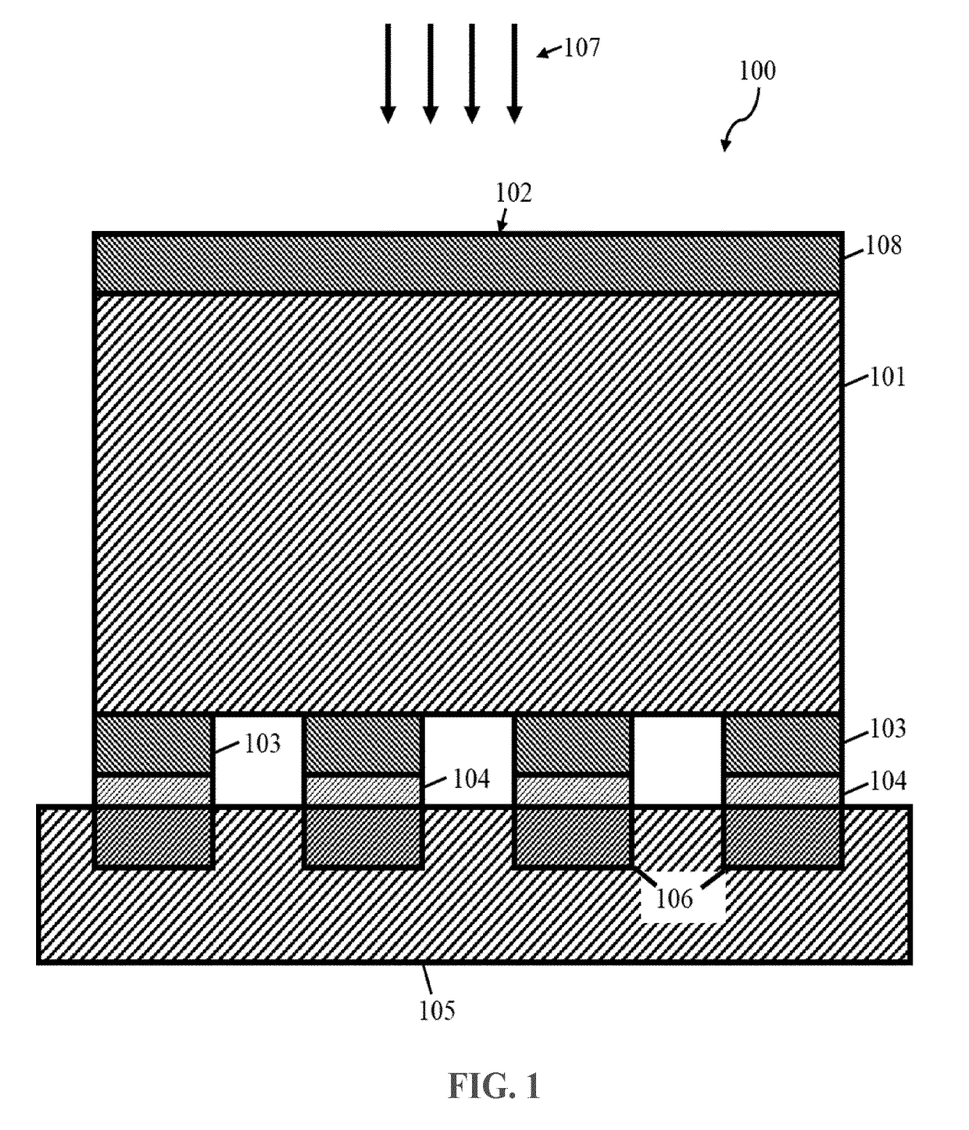
FIG. 1 is a schematic illustration of a radiation detector.

FIG. 1 is a schematic illustration of an embodiment of a detector 100 comprising a top electrode 108, a bulk direct conversion material 101, a plurality of pixel electrodes 103 forming a structured bottom electrode, conductive attachment means 104 at least for each pixel electrode 103, and a substrate 105 (e.g. Si) which comprises pixel electronics 106. The bulk direct conversion material 101 may be thin, e.g. less than 3.0 mm, less than 2.0 mm, e.g. about 500 micrometer thick; its thickness depends on the material and is selected so as to provide sufficient absorption of radiation within its bulk volume, e.g. thicknesses achieving more than 50% photon absorption or, preferably, achieving more than 80% photon absorption. Non-limiting examples of direct conversion materials 101 suitable for converting impinging radiation such as X-rays directly into electric charges inside the bulk are alloys of cadmium zinc telluride (CZT), cadmium telluride (CdTe), gallium arsenide, amorphous selenium, or other suitable direct conversion materials, preferably semiconductors comprising a high atomic number element. Other examples of direct conversion materials are silicon or germanium, which, apart from converting X-rays, are also suitable for converting ultraviolet or visible light. Direct conversion is herein understood to be a radiation conversion process that immediately results in the creation of a pair of electric charges, excluding intermediate conversion processes such as, for example, re-emission of light at longer wavelengths (luminescence). Each incoming beam of radiation, e.g. an X-ray beam comprising a plurality of polyenergetic photons, generates clouds of free charge carriers with the amount of free charges being proportional to the energy of the incident photons. It is an advantage of direct conversion materials that an incident radiation signal is directly converted into the charges to be detected, its DQE is not impaired by losses related to a re-emission of radiation (scintillation) such as quenching, light guiding and collection losses, etc. In preferred embodiments of the invention the incident radiation 107 are X-rays which generate electron-hole pairs in a direct conversion semiconductor material, e.g. CZT. A radiation signal in the context of the present invention generally refers to a beam of radiation incident on at least a portion of the detector 100, e.g. a beam of X-ray photons, but it may particularly refer to a controlled beam of radiation, wherein beam control may comprise beam shaping (e.g. control of the divergence angle), spatial filtering of a beam emitted by a radiation source, spatial modulation (e.g. by locally absorbing materials) and/or temporal modulation (e.g. on/off switching, pulse trains) of the beam of radiation, etc. Hence, a radiation signal may be provided, for example, if a radiation source (e.g. X-ray source) is powered and a may not be provided any longer if this radiation source is turned off.

The detector 100 includes a top electrode 108, a first major surface of which forms the detector top surface 102, and a second major surface of which is in contact with the bulk direct conversion material 101. This top electrode 108 typically is a thin, unstructured, flat electrode which minimally absorbs the radiation 107 incident on it. A bottom electrode is structured as an array of pixel electrodes 103, for example as a regular or irregular pattern of a plurality of pixel electrodes, for example a pattern of square pixel electrodes defining the active pixel regions of the detector 100. The bottom electrode, however, is not limited to an array of square pixel electrodes 103, and circular pixel electrodes, hexagonal pixel electrodes, or sets of vertical and horizontal stripes on slightly offset planes with respect to the thickness of the bulk direct conversion material are further non-limiting examples thereof. An array of pixel electrodes 103 may have a pixel pitch of 1.0 mm or less, e.g. 500 micrometer or less, or 200 micrometer or less, depending on the targeted spatial resolution, energy resolution, and collected signal strength, typical exposure times, etc. A detector 100 may for example include, without being limited to these particular choices, an 8×8, a 16×16, or a 32×32 array of pixel electrodes 103. The plurality of pixel electrodes 103 are each electrically connected to pixel electronics 106 by suitable conductive attachment means 104. Such conductive attachment means 104 may for example comprise wires, gold studs, solder bumps, indium bumps, etc., which allow the bulk direct conversion material 101 with the patterned bottom electrode to be bonded to a top surface, for instanced a flat top surface, of a substrate 105 whereby an electrical connection is established between each of the pixel electrodes 103 on the one side and each of the pixel electronics 106 on the other side. A substrate 105 which comprises pixel electronics 106 may, for example, be a semiconductor chip, e.g. a CMOS chip, and the plurality of pixel electronics 106 may for example be part of an integrated circuit manufactured into or onto a semiconductor chip, for instance an ASIC (Application Specific Integrated Circuit).

Multiple detectors 100 may be used concurrently in a detector assembly to increase the field of view or radiation 107 sensitive surface area of detection without scarifying spatial resolution. For instance, a detector 100 may form a tile in a larger detector assembly comprising one, two, or more rows of these tiles, and each row may comprise many tiles, e.g. 8, 16, 32, or more tiles. A detector assembly may have its tiles attached to a flexible or rigid support, e.g. on a collection of tilted PCB boards.

During operation of the detector 100, a strong electrical field is generated inside the direct conversion material, for instance a negative potential is generally applied to the top electrode 108, e.g. the cathode, and a more positive potential is provided at the pixel electrodes 103 of the bottom electrode, e. g. the anode, whereby an electric field between top and bottom electrode is the result of the potential difference. Depending on the bulk direct conversion material 101 and its thickness, the potential difference may be a few volts only, tens of volts, or even hundreds of volts. For CZT crystals as bulk direct conversion material 101 in particular embodiments, the potential difference may range between 100 V and 1500 V, depending on conversion material and thickness. Consequentially, the electric charge pairs generated, via the direct conversion of impinging radiation 107 inside the bulk direct conversion material 101, are split and the positive and negative charges are collected at the respective electrodes, e.g. electrons at the anode and holes at the cathode, in which an electrical current is induced. This implies that the detector 100 is operated in a photoconductive mode. Radiation 107 is incident on a top surface 102 of the detector 100, preferably at ninety degree angles to avoid cross-talk between active pixel regions of the detector 100, and comprises X-ray photons in preferred embodiments of the present invention, but is not limited thereto. Gamma rays, soft X-rays, extreme ultraviolet light, visible light, or infrared light are also examples of radiation 107, the type of radiation 107 being application specific. Highly integrated pixel electronics 106 transform the charge pulses into voltage pulses with a duration of for instance a few nanoseconds that can be counted digitally. It is not only possible to register or count each individual photon, but also to measure the energy from each individual photon, for instance in a dual-energy or multi-energy detection.

The charge generation process may also occur spontaneously in situations in which the detector 100 is not exposed to radiation 107. This causes a constant background dark current collected at the respective electrodes. If the bulk direct conversion material 101, e.g. the CZT crystal, has imperfections, e.g. trapping centers, or any other type of inhomogeneity, the local dark currents detected at each pixel electrode 103 will be different. Additionally, there may also exist some residual leakage currents in the temporal domain, caused, for example, by trapping and release of migrating charge carriers or incomplete charge removal immediately after exposure, which may create ghost images, band artefacts, etc., at the time of image reconstruction, e.g. for direct viewing on a display in a CT scanner. Dark currents are only one form of leakage currents that lead to higher (shot) noise levels limiting the dynamic range of the detector and broadening its spectral response. Other forms of leakage currents include leakage currents due to charges migrating through the capacitive structure formed by the top and bottom electrodes of the detector 100, charge trapping release, charge injection, etc. Also temperature increases or a temperature gradient across one single detector 100 or across tiles, in a detector assembly including many detector tiles, may induce a drift of leakage currents. Besides, pixel electronics 106 may also have non-negligible offset currents (input leakage) at their respective input nodes which are temperature dependent, depending on circuit topology and implementation. Together, all these leakage currents ultimately contribute to a detectable coherent energy shift of the readout pixel electronics 106. A coherent shift in energy or a coherent drift of the average leakage currents, in the context of the present invention, means that the average shift/drift across all pixels has a non-zero average. That is, if for example temperature changes in one direction, all pixels will increase/decrease an average leakage current in one and same direction. Typically, the leakage currents evolve on timescales which are much slower than the (charge) pulse dynamics of the detector 100 and, consequentially, are generally considered to be dc or low frequency components of the detector signal. This generally affects the energy resolution of the detector 100 as the baseline is shifting in an often unpredictable way, thus compromising the pulse height measurements, and ultimately image quality and accuracy of imaging information. For example, changes in leakage currents smaller than 1 nA per detector 100, e.g. per pixel electrode, if left uncorrected or if not compensated for, may lead to band artefacts in reconstructed CT images, whereas leakage currents may increase to tens of nA, also due to aging effects, humidity, etc. Therefore it is important to take into account inhomogeneous leakage currents and their temporal drifts as accurately as possible. For a CT scan this may be achieved by measuring the leakage currents across a detector 100, or across many detectors in a detector assembly, before the scan starts. As the CT scan progresses, a multitude of projections of the scanned object require a multitude of exposures of the detector 100, which may be part of a detector array in a detector assembly. As each exposure to the incident radiation deposits some energy inside the detector 100, the temperature at the detector 100 may be significantly increased after the many projections of a CT scan, e.g. a temperature of the detector 100 may increase linearly or even exponentially during the scan. Therefore, it is preferred to also measure leakage currents after every completed scan. However, the moments at which a measurement of the leakage currents of a detector 100 is performed are not limited to before/after each scan and may optionally be performed during the scan, e.g. at regular time intervals during the scan when a switching tube is off. The use of switching tubes is known in the related art.

In some embodiments of the invention, the pixel electronics 106 include leakage current detection and compensation circuits, e.g. an ASIC with a leakage current detection unit and compensation unit, which partially compensates for time-variant leakage currents. However, compensating leakage currents by the sole means of an ASIC proves difficult since ASICs are typically designed for target specifications, e.g. range and resolution, which is in conflict with the large variety of existing direct conversion materials, e.g. a large variety of process dependent samples of CZT crystals, which makes a universally matched design impossible. Aging effects of a CZT crystal, radiation damage, lower quality CZT crystals, or high radiation rates may also negatively impact such an approach as the leakage currents may grow beyond the designed specification or a designed resolution may not be fine enough to avoid quantization errors and the emergence of artefacts.

In some embodiments of the invention, a guard ring applied to the side faces of the bulk direct conversion material 101 is limiting the drift of charge carriers to the side faces of the detector where they may experience increased trapping or surface currents. A steering grid for avoiding pixel cross-talk may also be implemented between the pixel electrodes 103, preferably on a layer which insulates them from the pixel electrodes 103. An anti-scatter grid or other radiation absorption controlling layers may be provided optionally above or on top of the detector 100, whereby coherent radiation scatter incident at angles different from ninety degrees is reduced or an incident radiation dose is adjusted.

In alternative embodiments of the invention, the direct conversion material is not a bulk unit but is patterned too, for example into pixel columns and each pixel column includes a top and a bottom electrode.

Figure 2:
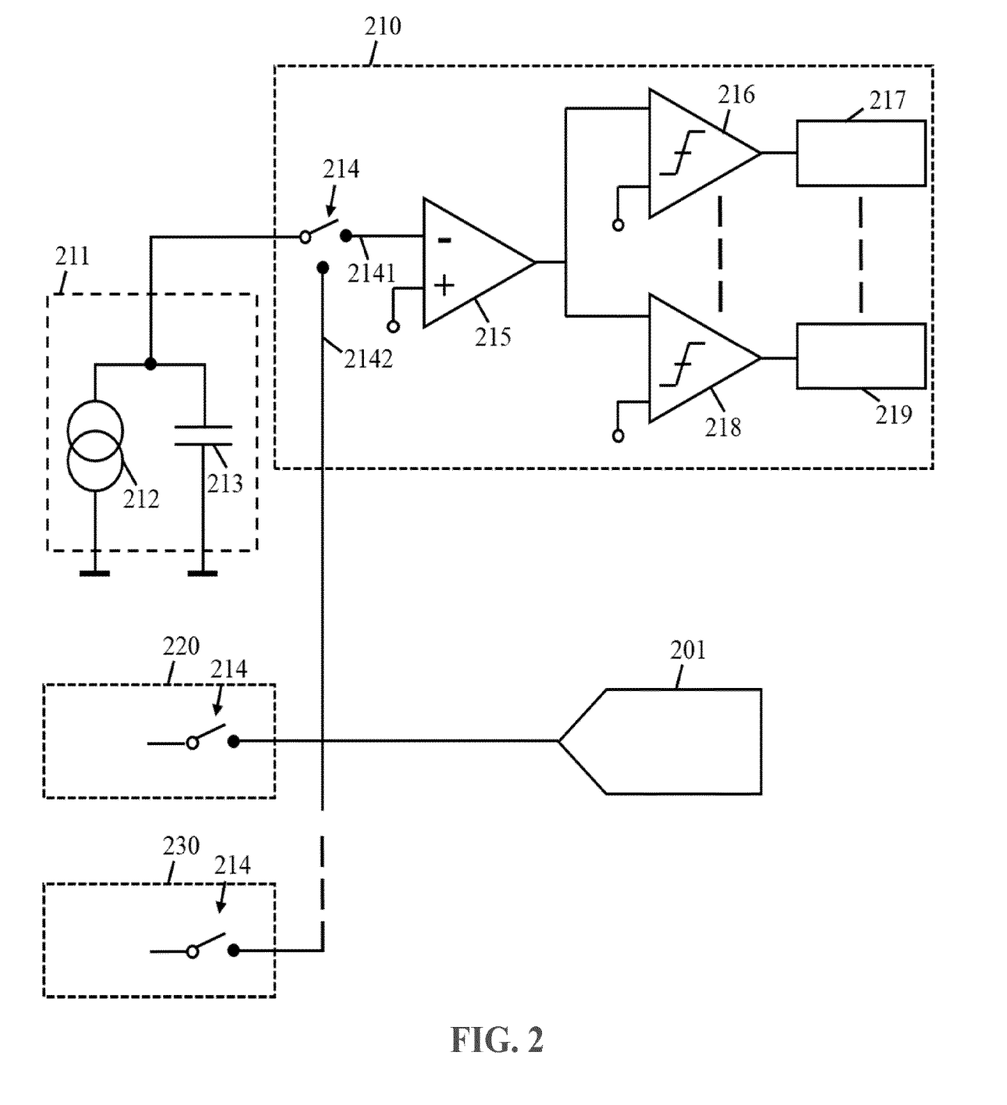
FIG. 2 shows an exemplary electronic block diagram of pixel electronics according to an embodiment of the invention.

FIG. 2 shows an exemplary electronic block diagram of pixel electronics 106 according to an embodiment of the invention, which can be used with a detector 100, for instance as illustrated in FIG. 1 or a variant thereof. An equivalent circuit 211 for the charge carrier generation and collection process, which occurs within the bulk direct conversion material 101 and at pixel electrodes 103 or at the top electrode 108, is included in the drawing of FIG. 2 for completeness and ease of description, but is not part of the pixel electronics 106 contained in or on the substrate 105.

The equivalent circuit 211 models, for each pixel of the detector, the generation and migration of charge carriers, caused by an impinging radiation signal received at this pixel, as an equivalent current source 212. This equivalent current source 212 also generates the leakage currents associated to this pixel. Each pixel also has an associated input capacitance 213 which, in a first approximation, is formed by the respective pixel 103 electrode and top electrode 108.

As shown in FIG. 2, the charge signal collected at a single pixel electrode 103 during exposure of the detector 100 is processed in a single signal processing chain 210 associated with this particular pixel electrode, i.e. by means of the respective conductive attachment means 104, and is referred to as pixel signal processing chain 210. Each pixel has its own signal processing chain 210, 220, 230. Each pixel signal processing chain 210, 220, 230 includes a switching element 214 connected to the equivalent current source 212. Each switching element 214 is configured for switching between a first signal path 2141 and a second signal path 2142 associated with the corresponding pixel signal processing chain 210, 220, 230. For every pixel, the first signal path 2141 connects the current source 212, via the switching element 214, with the input of a readout unit. The readout unit may comprise a front-end circuit 215, in which case first signal path 2141 connects the current source 212, via the switching element 214, with the input of the front-end circuit 215. A front-end circuit 215 may include a pre-amplifier stage, e.g. a charge-sensing amplifier (CSA), and a pulse shaper, both of which may be programmable, e.g. programmable in gain, bandwidth, or pulse shaping time constants. The output of the front-end circuit 215 is connected to a plurality of discriminators also included in the readout unit, e.g. two discriminators 216, 218 as illustrated in FIG. 2, with different, e.g. adjustable, threshold settings. In each of the discriminators 216, 218, the output of the front-end circuit 215 is compared to the threshold, and signal pulses above the threshold are registered in a corresponding counter 217, 219 connected to the particular discriminators 216, 218. The counters 217, 218 are also included in the readout unit.

For every pixel, the second signal path 2142 connects the current source 212, via the switching element 214, with the input of a current measuring device 201, e.g. an analog-to-digital converter The analog-to-digital converter may be implemented in the same substrate 105 (e.g. Si) as the pixel electronics 106, e.g. as part of an ASIC. Alternatively, the current measuring device 201 may be a transimpedance amplifier. Its resulting analog output of the current measured at its input may be converted subsequently by an analog-to-digital converter which may be implemented in the same substrate 105 (e.g. Si) as the pixel electronics 106 or may be external to it. As shown in FIG. 2, the at least one current measuring device 201, e.g. an analog-to-digital converter, may receive input from more than just a single pixel, via signal processing chains 210, 220, 230, i.e. the inputs of several pixel signal processing chains can be summed at the input of a shared current measuring device 201, e.g. at the input of a shared analog-to-digital converter. First and second signal paths 2141, 2142 of each pixel signal processing chain 210, 220, 230 are well isolated from each other. In accordance to embodiments of the invention, the switching elements 214 ensure that readout units, e.g. front-end circuits 215, etc., on the first signal paths 2141 are actively disconnected when a leakage current measurement is performed at the input of the at least one current measuring device 201. Therefore, charge flows into input nodes of the readout units, e.g. into the front-end circuits 215, are efficiently prevented to not distort the leakage current measurements. In the context of the present invention, actively disconnecting the first signal paths 2141 by means of the switching elements 214 may considered achieved if the off-resistance value of a switching element 214 towards a connected input of a readout unit, e.g. a front-end circuit 215, is considerably higher than the combined resistance value of the on-resistance value of that switching element 214 plus the input impedance of the at least one current measuring device 201, e.g. the analog-to-digital converter. A person skilled in the art will know how to design or select particular switching elements 214.

Prior to performing a radiation measurement, the detector 100 may be configured in a leakage current measurement enable mode. Upon receipt of an enable signal, the switching elements 214 of a cluster of pixels will be steered to the second signal path 2142, the remainder of the pixels of the detector staying connected to their readout units, e.g. connected to the input of the front-end circuit 215, along the first path 2141. A processor or suitable signal processing unit may provide the appropriate enable signals to the switching elements 214. This processor or signal processing unit may be external to the detector 100 or may be included in it, e.g. a processor or signal processing unit which is implemented in the same substrate 105 (e.g. Si) as the pixel electronics 106, e.g. as part of an ASIC. A cluster of pixels may comprise at least two pixels of the detector 100, preferably more than two pixels, e.g. more than ten pixels. A cluster of pixels may even comprise all the pixels of the detector 100. Different spatial distributions for the cluster of pixels exist, or there may exist more than one cluster of pixels, e.g. two or more clusters of pixels independent from each other. In some embodiments of the invention, for instance, all the edge pixels of the detector 100 may be clustered together, or its complement, that is all the bulk pixels of the detector 100 not located at a detector edge may be clustered together. In other embodiments of the invention, scattered spatial pixel distributions may form a cluster, for example a random selection of pixels of the detector 100 or a regular pattern, e.g. checkerboard pattern; the cluster in both cases comprising contributions from different locations of the array of pixel electrodes 103. In yet other embodiments of the invention, many small clusters of pixels may be formed and selected/enabled independently from each other, e.g. two-by-two pixel electrode sub-arrays as part of the larger array of pixel electrodes 103 and many such sub-arrays covering the whole array, or clustering pixels of each quadrant of a square or rectangular array of pixel electrodes 103 together. In each of these embodiments, the current measuring device 201, e.g. analog-to-digital converter, receives a current input from more than just a single pixel signal processing chain 210, 220, 230, and all the current inputs are summed at its input node. As the leakage current measurement is enabled prior to a radiation detection, only leakage currents are summed and averaged by the current measuring device 201, e.g. summed and averaged by the analog-to-digital converter. The average leakage current measured at the current measuring device 201, e.g. the analog-to-digital converter, corresponds to the average leakage current measured across the currently enabled cluster of pixels. To devise a correct average leakage current per pixel for the cluster of pixels, the processor or suitable signal processing unit may provide the information for or perform the weighting of the summed leakage current, measured by the current measuring device 201, in agreement with the number of selected/enabled pixels in that cluster. For this purpose the detector 100 or external software/hardware may store cluster patterns for pixels and their associated pixel count. Such an average leakage current measurement may be repeated for the same or different clusters of pixels prior to each radiation detection. This has the advantage that a noise level for the leakage current measurement may be decreased and the precision of this measurement may be increased. It is an advantage of some embodiments of the invention that only a single current measuring device, e.g. a single analog-to-digital converter, is required. In alternative embodiments of the invention, more than one current measuring device 201 but less than one current measuring device 201 per pixel is provided. Therefore, multiple clusters of pixels may be enabled simultaneously and their corresponding per pixel average leakage currents measured independently by connecting their second signal paths 2142 to the respective current measuring devices 201. This reduces the circuit design complexity at each pixel and for each pixel processing chain 210, 220, 230, i.e. a dedicated current measuring device 201 per pixel is not required but only one or a few current measuring devices 201 for the full pixel array of the detector 100. Moreover, the measurement of an average leakage current at a current measuring device 201, e.g. at an analog-to-digital converter, is using the current inputs of all enabled pixels of the cluster, therefore larger current signals, as compared to a single pixel measurement, are obtained at a current measuring device 201 which can have a simple design, e.g. a resolution of the analog-to-digital converter may be reduced (averaging effect) and the operation bandwidth of the analog-to-digital converter may also be reduced as only a single measurement per pixel cluster may be sufficient.

In embodiments in which the detector 100 is used in imaging applications, the measured average leakage currents per pixel may be embedded in the image data obtained for a radiation scan, e.g. embedded in the spectral image data (e.g. counts of the energy-discriminating channels) of a spectral CT scan. In addition thereto, or alternatively, the converted digital result obtained by the current measuring device 201 may be stored and accessed in a storage device, e.g. an internal register comprised in the electronic circuitry of the substrate 105.

In embodiments in which the detector 100 is used in conjunction with calibration or reference data, e.g. a spectral phantom in spectral CT, a leakage current measurement may be performed for this calibration or reference data too, and may be used in subsequent radiation detection measurements to estimate an equivalent energy shift with respect to this calibration or reference data. According to some embodiments of the invention, an average leakage current value obtained in a calibration step may be stored on the detector 100, e.g. in the detector 100 hardware implemented in the same substrate 105 (e.g. Si) as the pixel electronics 106, e.g. as a register of an ASIC. This stored value may be used to correct (in hardware) for deviation with respect to subsequent measurements, e.g. by establishing the difference and subtracting an average leakage current per pixel. For an array of detectors 100, e.g. for a detector assembly, an average leakage current value obtained in a calibration step may be stored for each individual detector 100 of the array separately. Such on-chip embodiment has the benefit that it may avoid post-acquisition correction steps.

In embodiments in which the detector 100 is used in conjunction with a spectral detector model for image reconstruction, e.g. in projection-based, iterative spectral CT implementing material decomposition, a spectral detector model which otherwise would lead to erroneous results, may be corrected for spectral energy shifts based on average leakage current measurements obtained for at least one pixel cluster, e.g. by adjusting threshold values in a spectral model, e.g. in a forward model which corrects counts induced by the equivalent energy shifts.

In embodiments of the invention, threshold values of the discriminators 216, 218 of each pixel processing chain 210, 220, 230 may be adjusted as a result of an average leakage current measurement performed for a cluster of pixels. In addition thereto, or alternatively, the counts obtained at counters 217, 219 of each pixel processing chain 210, 220, 230 may be adjusted as a result of an average leakage current measurement performed for a cluster of pixels.

According to a preferred embodiment of the invention, a leakage current measurement may be performed prior to each radiation measurement, e.g. prior to a CT scan of an object or patient. Preferably, another leakage current measurement is performed directly after each radiation measurement. This allows for an accurate estimation of the leakage currents and equivalent energy shifts that occurred during a radiation measurement protocol, e.g. during a full CT scan. However, embodiments of the invention are not limited to a single prior and/or single posterior leakage current measurement. Indeed, multiple repetitions of leakage current measurements may be performed for a single and/or multiple clusters of pixels before or immediately after each radiation measurement protocol, e.g. before or immediately after each CT scan. Additionally, some embodiments of the invention may also perform leakage current measurements during the radiation measurement protocol (e.g. during the multiple projections of a CT scan), e.g. by way of switching off the radiation incident on the detector 100 at regular time intervals, e.g. by using scanning systems with switching tubes.

According to some embodiments of the invention, fast models such as linear interpolation may be used to estimate average leakage currents for points in time that lie within the duration of a radiation measurement protocol, e.g. to estimate an average leakage current per pixel for some or all projections of a full CT scan. However, quadratic, cubic, or spline interpolation methods may also be implemented and may constitute other non-limiting examples for interpolation. Alternatively, more advanced accurate estimation of the average leakage currents and equivalent energy shifts that occurred during the time of a radiation measurement protocol, e.g. during an integration period of a single radiation measurement, e.g. during a single projection of a full CT scan, may involve taking into account the full radiation flux history, e.g. X-ray flux history, of each individual pixel or of one or more clusters of pixels.

Figure 3:
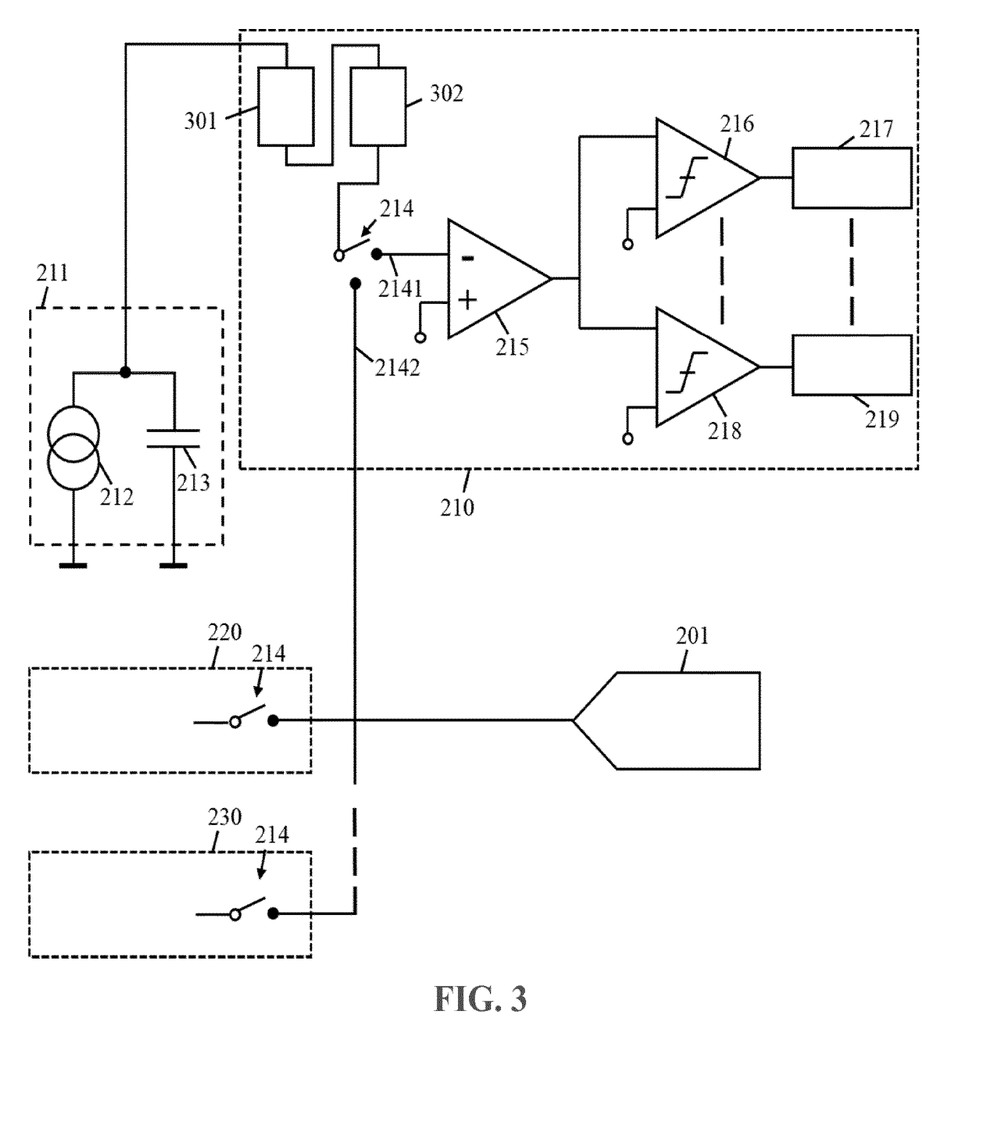
FIG. 3 shows an exemplary electronic block diagram of pixel electronics according to another embodiment of the invention implementing partial leakage current compensation.

In preferred embodiments of the invention, each radiation measurement protocol (e.g. CT scan comprising a plurality of angular projections) carried out by the detector 100 is accompanied by a leakage current estimation. This leakage current estimation may comprise temporal interpolation in a before/after configuration for the average leakage current measurements or/and may comprise spatial interpolation for a subsampling of the detector pixels by one or more different pixel cluster configurations, e.g. spatially interpolating the average leakage current value of every second pixel for a checkerboard pattern as a clustered measurement of the leakage currents of many pixels of the detector 100. In a further embodiment of the invention as illustrated in FIG. 3, some or all pixel processing chains 210, 220, 230 may include a leakage current detection unit 301 and a leakage current compensation unit 302. The leakage current detection unit 301 is operatively coupled to a pixel electrode 103 of the detector 100 and to the leakage current compensation unit 302. An output of the leakage current compensation unit 302 is operatively coupled to an input of the readout unit, e.g. coupled to an input of the front-end circuit 215. In such embodiments, the outputs of the leakage current compensation unit 302 of some or all pixel processing chains 210, 220, 230 may again be clustered together via switching elements 214 and summed at an input to the at least one current measuring device 201, e.g. an input to the at least one analog-to-digital converter. This is particularly advantageous in cases for which the detector 100 already provides a pre-compensation for leakage currents, but this pre-compensation is too inaccurate, e.g. inaccuracies resulting from digital-to-analog converters included in the leakage current compensation units 301 which always have some degree of quantization error. Therefore, the compensating current may only be controlled within given limits of precision, the limits depending on the design efforts, design space availability, cost, etc., such that the leakage current pre-compensation is generally imperfect and residual currents persist. In embodiments of the invention, the digital-to-analog converters for leakage current compensation are not required to be very precise as the average residual leakage current per pixel, e.g. less than 1 nA, is still measurable, for one or more pixel clusters, by the at least one current measuring device 201. It is an advantage of embodiment of the invention that designs in which the digital-to-analog converters cover the specifications of typical bulk direct conversion materials, e.g. a range CZT crystals, the at least one current measuring device 201, e.g. the at least one analog-to-digital converter, allows for a still wider range of specifications as residual and excess leakage currents are measured and taken into account. This is particularly relevant for avoiding failure by aging-induced, overly high leakage currents of the detector 100.

Figure 4:
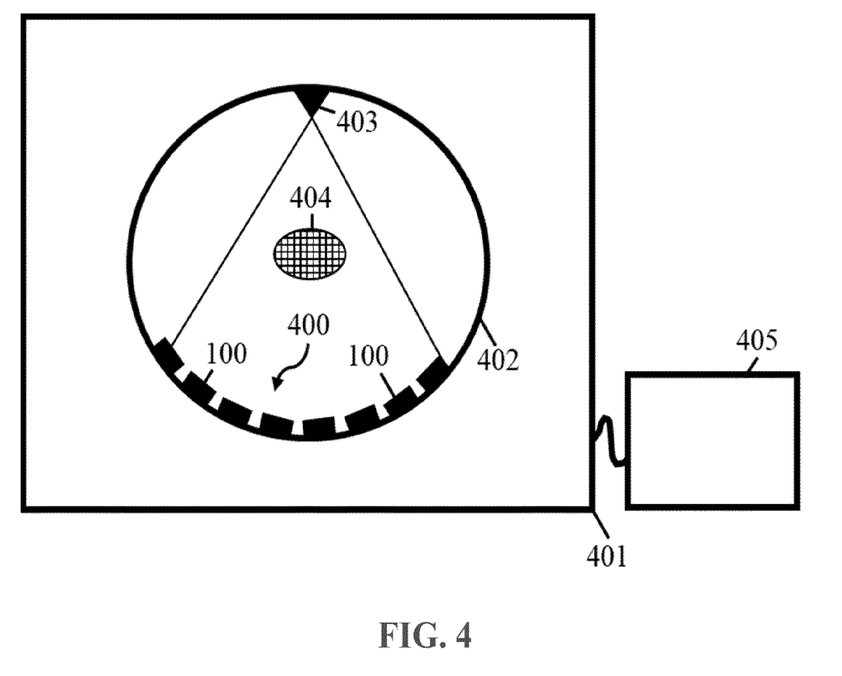
FIG. 4 is a schematic illustration of a scanning system comprising a plurality of radiation detectors according to an embodiment of the invention.

The present invention also relates to a detector system 400, e.g. an array of detectors 100, and a scanning system 401 comprising the same. FIG. 4 schematically depicts a CT scanning system 401 comprising a plurality of radiation detectors 100 arranged on a curved surface of a rotatable gantry 402. A radiation source 403, e.g. a switchable X-ray source operating at two or more different energies, is positioned opposite to the detector system 400 and secured to the rotatable gantry 402. Radiation 107, e.g. X-rays, emitted by the radiation source 403 is detected in the energy spectral domain by the detectors 100 of the detector system 400 after having propagated through a scan region in which an object or patient 404 is present. The object or patient 404 interacts with the radiation, e.g. by scattering or absorbing the radiation 107 and different sections of the object or patient 404 may be moved with respect to the rotatable gantry 402 such that a plurality of slices and projections at different angles may be obtained by the CT scanning system 401. An image reconstruction unit 405 may be connected to the scanning system 401 or may be part thereof. The image reconstructing unit 405 is suitable for reconstructing images of the scanned object or patient 404, e.g. it comprises processing means that reconstruct the images based on a projection dataset, e.g. based on an iterative spectral forward algorithm. According to embodiments of the invention, each detector 100 of the detector system 400 may be adapted to perform one or more leakage current measurements for clusters of pixels at least before and/or after each scan. These one or more leakage current measurements may be measurements of residual leakage currents obtained after leakage current compensation has been carried out. Image raw data obtained by the CT scanning system 401 is transmitted to the image reconstruction unit 405 and may also include the measure average leakage current values. Therefore, the image reconstruction unit 405 may use this information to correct for spectral shifts to improve image quality and/or avoid artefacts, e.g. by correcting the threshold value settings for the different energy windows/channels in a spectral forward model. A display unit for visualizing the reconstructed images may be provided in addition to the scanning system 401.

While the invention has been illustrated and described in detail in the drawings and foregoing description, such illustration and description are to be considered illustrative or exemplary and not restrictive. The foregoing description details certain embodiments of the invention. It will be appreciated, however, that no matter how detailed the foregoing appears in text, the invention may be practiced in many ways. The invention is not limited to the disclosed embodiments.

Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A radiation detector configured for detecting leakage currents, comprising:
   a direct conversion material for converting incident radiation into charges, the direct conversion material having a first major surface and a second major surface;
   at least one first electrode connected to the first major surface of the direct conversion material and a plurality of second electrodes connected to the second major surface of the direct conversion material, each electrode of the at least one first electrode and the plurality of second electrodes being arranged for collecting charges generated in an electric field applied between the first and the second electrodes;
   at least one shared current measurement device; and
   a plurality of signal processing chains, each signal processing chain of the plurality of signal processing chains comprising:
      a discriminator configured to discriminate between energy values with respect to the incident radiation; and
      a switch configured to:
         send a first signal on a first signal path electrically connecting one electrode of the plurality of second electrodes with the discriminator for discriminating between energy values; and
         send a second signal on a second signal path electrically connecting the one electrode of the plurality of second electrodes with an input to the at least one shared current measurement device;
   wherein the switches of the plurality of signal processing chains are configured to send, to the at least one shared current measurement device, the second signals from the plurality of second electrodes on the second signal paths for measuring a leakage current received at a corresponding plurality of second electrodes in the absence of incident radiation.

2. The detector according to claim 1, wherein the direct conversion material is a CZT crystal.

3. The detector according to claim 1, wherein the plurality of second electrodes are arranged as an array of electrodes on the second major surface.

4. The detector according to claim 1, further comprising a storage configured to store a measured leakage current.

5. The detector according to claim 1, wherein the at least one shared current measurement device comprises an analog-to-digital-converter.

6. The detector according to claim 1, wherein at least one signal processing chain of the plurality of signal processing chains further comprises:
   a leakage current detector; and
   a leakage current compensator for the first signal sent on the first signal path and for the second signal sent on the second signal path,
   wherein an output of the leakage current detector is connected to an input of the leakage current compensator, and
   wherein an output of the leakage current compensator is connected to the switch.

7. A detector system, comprising:
   a radiation source;
   an image reconstructor configured to reconstruct images of an object; and
   a plurality of radiation detectors, each radiation detector of the plurality of radiation detectors being configured for detecting leakage currents, each radiation detector of the plurality of radiation detectors comprising:
      a direct conversion material for converting incident radiation into charges, the direct conversion material having a first major surface and a second major surface;
      at least one first electrode connected to the first major surface of the direct conversion material and a plurality of second electrodes connected to the second major surface of the direct conversion material, each electrode of the at least one first electrode and the plurality of second electrodes being arranged for collecting charges generated in an electric field applied between the first and the second electrodes;
      at least one shared current measurement device; and
      a plurality of signal processing chains, each signal processing chain of the plurality of signal processing chains comprising:
         a discriminator configured to discriminate between energy values with respect to the incident radiation; and
         a switch configured to:
            send a first signal on a first signal path electrically connecting one electrode of the plurality of second electrodes with the discriminator for discriminating between energy values; and
            send a second signal on a second signal path electrically connecting the one electrode of the plurality of second electrodes with an input to the at least one shared current measurement device;
   wherein the switches of the plurality of signal processing chains are configured to send, to the at least one shared current measurement device, the second signals from the plurality of second electrodes on the second signal paths for measuring a leakage current received at a corresponding plurality of second electrodes in the absence of incident radiation.

8. The detector system according to claim 7, wherein the image reconstructor comprises a detector model which uses a measured leakage current for correcting spectral energy shifts.

9. The detector system according to claim 7, further comprising a display configured to display leakage current distributions of the plurality of detectors.

10. A method for detecting leakage currents in a direct conversion radiation detector, comprising:
    providing at least one first electrode connected to a first major surface of a direct conversion material and a plurality of second electrodes connected to the second major surface of the direct conversion material, each electrode of the at least one first electrode and the plurality of second electrodes being arranged for collecting charges generated in an electric field applied between the first and the second electrodes;
    converting collected charges to detection signals;
    process the detection signals by discriminating between energy values with respect to incident radiation with a plurality of signal processing chains, each signal processing chain of the plurality of signal processing chains comprising a discriminator for discriminating between energy values with respect to the incident radiation;
    sending a first signal on a first signal path electrically connecting one electrode of the plurality of second electrodes with the discriminator for discriminating between energy values, and sending a second signal on a second signal path electrically connecting the one electrode of the plurality of second electrodes with an input to one of the at least one shared current measurement devices;
    wherein the plurality of switches send, to the at least one shared current measurement device, the second signals from the plurality of second electrodes on the second signal path for measuring a leakage current received at a corresponding plurality of second electrodes in the absence of incident radiation.

11. The method according to claim 10, further comprising storing a measured leakage current.

12. The method according to claim 10, further comprising reconstructing images of an object to obtain projection data for radiation traversing the object.

13. The method according to claim 12, further comprising using a detector model which uses a measured leakage current for correcting spectral energy shifts.

14. The method according to claim 10, further comprising displaying leakage current distributions.

* * * * *